United States Patent [19]

Michaels

[11] Patent Number: 5,275,804
[45] Date of Patent: Jan. 4, 1994

[54] PROCESS AND COMPOSITION FOR ORAL HYGIENE

[75] Inventor: Edwin B. Michaels, Milford, Conn.

[73] Assignee: E. B. Michaels Research Associates, Inc., Milford, Conn.

[21] Appl. No.: 951,354

[22] Filed: Sep. 25, 1992

Related U.S. Application Data

[60] Continuation of Ser. No. 271,997, Nov. 15, 1988, abandoned, which is a division of Ser. No. 81,580, Jul. 31, 1987, Pat. No. 4,839,158, which is a continuation of Ser. No. 833,333, Feb. 25, 1986, abandoned.

[51] Int. Cl.$^5$ .............................................. A61K 7/22
[52] U.S. Cl. ...................... 424/54; 424/49; 424/52; 424/57; 514/900; 514/901; 514/902
[58] Field of Search ............... 424/49, 52, 57, 54; 514/900-902

[56] References Cited

U.S. PATENT DOCUMENTS

| | | | |
|---|---|---|---|
| 2,888,383 | 5/1959 | Byrne | 424/54 |
| 3,202,714 | 8/1965 | Zimmerer | 260/584 |
| 3,223,647 | 12/1965 | Drew | 252/137 |
| 3,976,765 | 8/1976 | Nachtigal | 424/54 |
| 4,062,976 | 12/1977 | Michaels | 514/561 |
| 4,075,350 | 2/1978 | Michaels | 424/316 |
| 4,093,711 | 6/1978 | Blackburne | 424/54 |
| 4,107,328 | 8/1978 | Michaels | 424/316 |
| 4,117,108 | 9/1978 | Shapiro | 424/54 |
| 4,130,637 | 12/1978 | Bauman | 424/54 |
| 4,145,436 | 3/1979 | Michaels | 424/273 |
| 4,183,952 | 1/1980 | Michaels | 424/65 |
| 4,209,504 | 6/1980 | Harth | 424/54 |
| 4,209,533 | 6/1980 | Gilbertson | 424/59 |
| 4,212,856 | 7/1980 | Hoyles | 424/52 |
| 4,213,961 | 7/1980 | Curtis | 424/54 |
| 4,215,144 | 7/1980 | Thiele | 424/318 |
| 4,219,541 | 8/1980 | Schmid | 424/54 |
| 4,490,353 | 12/1984 | Crawford | 424/54 |
| 4,528,182 | 7/1985 | Curtis | 424/54 |
| 4,839,158 | 6/1989 | Michaels | 424/54 |

OTHER PUBLICATIONS

Tanzer et al., Antimicrobial Agents and Chemotherapy, vol. 13, No. 6, 1044-1045, Jun. 1978.
Tanzer et al., Anlimicrobial Agents and Chemotherapy, vol. 12, No. 6, 721-729, 1977.
Corner, A. M. et al. Abstract 407 Journal of Dental Research vol. 65 Special Issue. 1986.
Dolan, M. M. et al. Abstract 411 Journal of Dental Research vol. 65 Special Issue 1986.
Corner, A. M. et al. Abstract 948 Journal of Dental Research vol. 65 Special Issue 1986.
Malamud, D. et al. Abstract 949 Journal of Dental Research vol. 65 Special.
Lindstedt, M. Antimicrobial Agents and Chemotherapy 34(10): 1949-1954 (1990).
Patent Abstracts of Japan, vol. 8, No. 71 (C-217) [1508], 3rd Apr. 1984; & JP-A-58 225 007 (Raion K.K.) Dec. 27, 1983.
Corner et al., Antimicrobial Agents and Chemotherapy, 350-353, Mar. 1988.
The Merck Index, 9th ed. Merck and Co. Inc. Rahway, N.J. 1976 No. 2418, p. 316.
Je Fopau/os Dentifrices, Noyes Data Corp., Park Ridge, N.J. pp. 65-67 (1920).

*Primary Examiner*—F. T. Moezie
*Attorney, Agent, or Firm*—Ladas & Parry

[57] ABSTRACT

A process for enhancing oral hygiene by reducing oral microflora and for inhibiting the formation of dental plaque by applying, to the oral cavity a composition containing (a)0.1 to 40 parts, by weight, of a higher acyl-N-betaine having the structure or where R is a higher alkyl group of from 10 to 18 carbon atoms, or mixtures thereof, and (b) 0.1 to 40 parts, by weight of a higher alkyl-N,-N-dimethylamine oxide, a higher alkyl-N-N-dihydroxyethylamine oxide, or an acyl-amino t-amine, of the respective structures:
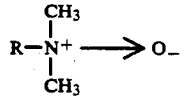
-continued
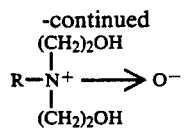
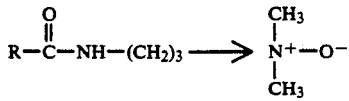
10 Claims, 1 Drawing Sheet

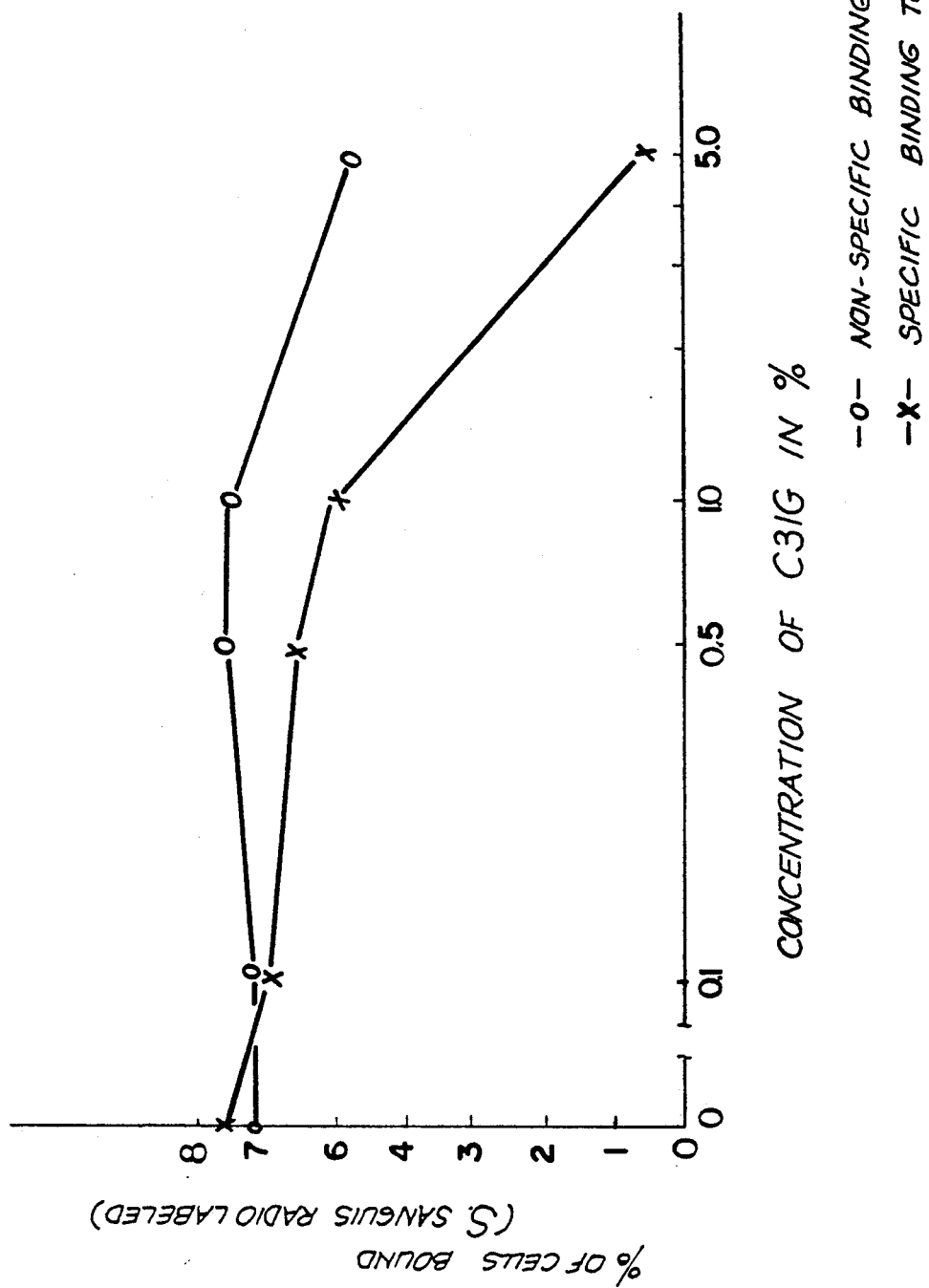

Page 1

PROCESS AND COMPOSITION FOR ORAL HYGIENE

This is a continuation of copending application(s). Ser. No. 07/271,997 filed on Nov. 15, 1988, now abandoned which is a divisional of application Ser. No.: 07/081,580 filed Jul. 31, 1987, now U.S. Pat. No. 4,839,158, which is a continuation application of Ser. No.: 06/833,333 filed Feb. 25, 1986, now abandoned.

BACKGROUND OF THE INVENTION

1. Field of the Invention

The present invention relates to a process for enhancing oral hygiene by removing and preventing plaque and calculus which comprises utilizing a mixture of certain amines in a pharmaceutically acceptable carrier. More particularly, the invention is concerned with a method for employing mixtures of an acyl-N-betaine and amine oxides, more particularly an acylamido-t amine oxide, more specifically defined hereinbelow, in reducing oral microflora without staining tooth enamel. Further, the invention comprises a novel composition when it is incorporated into a dentifrice.

2. Description of the Prior Art

It is known that certain mixtures of amines are effective antimicrobials. For instance, the art is aware of certain antimicrobial compositions comprising an alkyl-N-betaine, an alkyl-N-sulfobetaine, an acyl betaine, or an N-alkyl substituted alanine-2-aminopropionic acid or an in admixture with an alkyl-N, dihydroxyethyl amine oxide. There is no disclosure therein that the compositions of the art are useful as an oral hygiene aid. However, as is further known, the antimicrobial activity of simple, alkyl betaines disclosed for instance in U.S. Pat. No. 4,130,637 is less than one-tenth that of related cationic quaternary ammonium salts. See R. L. Stedman et al, J. Appl. Microbiology, 1,142, (1953). Such a simple betaine alone does not possess any anti-plaque properties. The carboxylate group must be separated from the quaternary nitrogen by as many as 10 methylene groups to confer anti-plaque activity. If a simple betaine could be employed as an oral hygiene additive to avoid staining and minimize plaque formation, such a provision would fulfill a need well recognized in the art.

SUMMARY OF THE INVENTION

In accordance with the process of the invention, it has been unexpectedly found that certain hereinbelow defined betaines, in combination with higher fatty amine oxides, are effective antimicrobials and inhibit the growth of plaque in vivo, and unlike other antimicrobials, do not stain teeth. The anti-staining, anti-plaque composition can be employed in, for instance, a mouthwash or oral rinse as well as in tooth cleaning preparations, employing pharmaceutically acceptable carriers such as gelling agents, polishing agents, flavorings, binders and equivalents thereof. When the admixture of amines is combined with certain specific polishing agents, as defined below, the invention comprises a novel composition for use in oral hygiene.

DESCRIPTION OF THE DRAWING

Figure—A graph demonstrating the effect of C31G on bacterial adhesion to tooth surfaces.

DETAILED DESCRIPTION OF THE INVENTION

The effective component of the composition employed in the process of the invention as an oral hygiene aid consists essentially in admixture of: (a) the alkyl-N-betaine, alkyl-N-sulfobetaine, acyl-N-betaine, alkyl N-substituted aminopropionic acid or an alkylimidazolinium betaine and (b) the alkyl-N, N-dimethylamine oxide, alkyl-N, N-dihydroxyethylamine oxide or acylamide t-amine oxide. The components (a) and (b) are usually admixed at a temperature ranging from 25° C. to 80° C. in a substantially aqueous or nonaqueous environment and acid is then added in an amount necessary to adjust the pH of a 0.5% solution to 7.5, and below to as low as 4.5. The result is a substantially uniform, homogeneous, relatively nontoxic composition having enhanced broad spectrum activity against oral bacterial and fungal pathogens.

The alkyl-N-betaine, the alkyl-N-sulfobetaine, the acyl-N-betaine, the alkyl N-substituted 2-aminopropionic acid and alkylimidazolinium betaine (also referred to as codoamphoacetates) employed as the components (a) of the composition of the invention have structures, respectively, as follows:

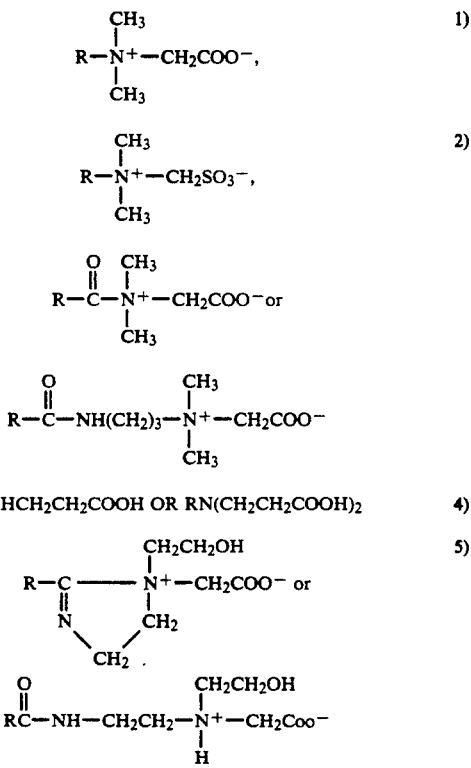

where R is a higher alkyl group having from 10 to 18 carbon atoms.

Illustrative of these aforementioned substances are; 1) coco-N-betaine, cetyl-N-betaine, stearyl-N-betaine, isostearyl-N-betaine, oleyl-N-betaine; 2) coco-N-sulphobetaine, cetyl-N-sulphobetaine, stearyl-N-sulfobetaine, isostearyl-N-sulfobetaine, oleyl-N-sulfo betaine; 3) cocoamido-N-betaine, cetylamido-N-betaine, stearylamido-N-betaine, isostearylamido-N-betaine, oleyl-amido-N-betaine; 4) N-coco-2 aminopropionic acid, N-cetyl-2-aminopropionic acid, N-stearyl-2-aminopropionic acid, N-isostearyl-2-aminopropionic acid, N-oleyl-2-aminopropionic acid, N-stearyl-bis (2-aminopropionic acid), N-oleyl-bis (2-aminopropionic acid), N-coco-bis (2-aminopropionic acid), N-cetyl-bis (2-aminopropionic acid), (5) N-lauryl-bis (2-aminopropionic acid) 1-hydroxyethyl-1-carboxymethyl-2-decylimidazolium betaine; 1-hydroxyethyl-1-carboxymethyl-2-dodecylimidazolium betaine; 1-hydroxyethyl-1-carboxyethyl-2-cocoimidazolium betaine; 1-hydroxyethyl-1-carboxymethyl-2-stearylimidazolium betaine; 1-hydroxyethyl-1-carboxymethyl-2-oleylimidazolium betaine; or mixtures of the same.

There is some uncertainty as to the structure of the compounds sold as alkylimidazolinium. The alkylimidazolinium were previously thought to be ring structures by workers in the field. (See Ampholytic Cycloimidinium Surfactant, Koeber & Bloch, Soap Cosmetics/Chemical Specialties 1972, or Cosmetic Ingredient Dictionary, 3rd Ed., 1982). However, they are now believed to be linear (Estrin, N. F., Haynes, C. R. and Whelan, J. M. (Editors) (1982) Cosmetics Ingredient Descriptions Cosmetic, Toiletry and Fragrance Association, Inc. Washington, D.C.).

The (1) alkyl-N,N-dimethylamine oxide, (2) alkyl-N,N-dihydroxylethylamine oxide, or (3) acylamide t-amine oxide employed as component (b) of the aforementioned mixture, respectively, have the structure:

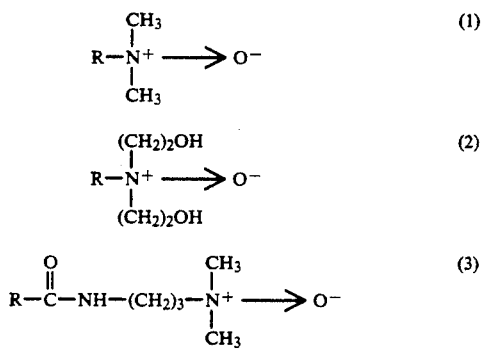

where R is a higher alkyl group of from 10 to 18 carbon atoms, for instance, radicals such decyl, undecyl, lauryl, tridecyl, myristyl, cetyl, stearyl, isostearyl or oleyl. Exemplary of the amine oxides are: decyl-N,N-dimethylamine oxide, lauryl-N,N-dimethylamine oxide, stearyl-N-N-dimethylamine oxide, oleyl-N,N dimethylamine oxide, coco-N,N-dihydroxyethylamine oxide, cetyl-N,N-dihydroxyethylamine oxide, oleyl-N,N-dihydroxyethyl-amine N,N-dihydroxyethylamine oxide, oleyl-N,N-dihydroxyethyl-amine oxide, and mixtures of the same.

In general, the acid necessary to supply the required pH to the overall composition can be any organic or inorganic acid which does not chemically react with the other components, such as hydrochloric acid, phosphoric acid, sulfuric acid, citric acid, acetic acid or nicotinic acid. The operating pH range for the composition is 4.5 to 7.5 and preferably, from about 4.5 to 6.5. The pH of an aqueous solution comprising the above enumerated components of the invention is determined by employing an aqueous solution of 0.5%, by weight, total of active components typically at a glass electrode, to precisely define the acidity of the composition.

In practice, the amounts of each of the components (a) and (b) of the overall composition can range widely from 0.1 part to 40.0 parts by weight. The balance after allowing for the acid is usually a physiologically acceptable solvent, such as water or a lower ($C_1$–$C_4$) monohydric aliphatic alcohol, for a total of 100 parts or more. Where water is employed, small amounts of a lower alkyl alcohol, such as ethanol or propanol, also may be added thereto to provide ease in formulation. The pH of the total composition is then adjusted to the requisite pH by adding a suitable inorganic or organic acid thereto. The defined components can be employed in mouthrinses, dental pastes, creams or tooth powders at concentrations ranging between 0.1 and 5.0% in a pH range from 4.5 to 7.5. Suitable nonreactive fluorides such as sodium fluoride or sodium monofluorophosphate also may be added.

When used against bacteria or fungi the composition of the instant invention may be applied directly to the surface to be protected, or dissolved in a pharmaceutical carrier before application. Typically an effective amount, i.e., 0.025 to about 10%, 0.25 to about 10%, by weight of the composition is included in an inert carrier. Alternatively, an effective amount e.g., 0.025 to about 10% by weight may be incorporated into a solid carrier such as polishing agents, flour and binding agents.

When compounds of the instant invention are prepared for oral use, they typically are incorporated in effective amounts up to about 10% by weight, preferably 0.05-3% by weight of the oral preparations. The oral preparation may be a liquid, such as a mouthwash. Mouthwash formulations typically contain 0-15% by weight of an aqueous lower aliphatic alcohol, such as ethanol, n-propyl alcohol or isopropyl alcohol. Alternatively, the oral preparation may be a dentifrice, dental cream or powder. In such cases, an effective amount, e.g., 0.025 to about 10% by weight, may be incorporated into a solid, inert carrier, for example, selective polishing agents, flour and binding agents.

The dentifrice also may include water, humectants such as sorbitol, propylene glycol, gelling agents, (Irish moss) and sodium carboxy methyl cellulose, preservatives, silicones, chlorophyll compounds, flavoring or sweetening materials and compounds which provide fluorine containing ions such as sodium fluroide and sodium monofluorophosphate. Some classes of polishing agents, other than silica or equivalent types, adversely affect the anti-plaque properties attributable to antimicrobial agents used in cleaning teeth. Such polishing agents may be Na $HCO_3$, $Al(OH)_3$ or soluble sodium metaphosphate when incorporated in formulations which show significant changes in pH after formulation. Silica-type polishing agents including, alumina (calcined), aluminum silicate, zeolites, calcium pyrophosphate, dicalcium acid phosphate, kaolin and other inert polishing agents also are useful in this invention. Thus, when the composition is a dentifrice containing an silica or equivalent type polishing agent, the dentifrice comprises a novel composition. As defined herein an inert polishing agent is one which is not reactive with the active ingredient surfactants of this disclosure nor with the protonating agents used for pH control and will not detract from the effectiveness of the dentifrice.

The particularized polishing agents selected for use in combination with the above defined betaines and fatty amine oxides in admixture, are particularly effective in reducing plaque compared with each of the components in oral compositions. The oral preparations of the instant invention are typically applied to the oral cavity by brushing the teeth or rinsing the oral cavity at least with a mouthwash or irrigation device twice daily for about 10-90 seconds. Typical oral preparations of the invention which can be applied in this manner are set forth in the Examples described below.

The betaines and fatty acid amine oxides of this invention are singularly effective when compared with other known antimicrobials. The effectiveness of the components of the present invention are set forth in U.S. Pat. No. 4,183,952 issued Jan. 15, 1980, U.S. Pat. No. 4,062,976 issued Dec. 13, 1977, U.S. Pat. No. 4,075,350 issued Feb. 21, 1978, U.S. Pat. No. 4,107,328 issued Aug. 15, 1978 and U.S. Pat. No. 4,145,436 issued Mar. 20, 1979, incorporated hereby by reference, as well as in the Tables and Examples.

To be effective as a mouthwash or irrigation formulation a composition must retain its stability and antimicrobial activity over the wide range of concentrations encountered at varied sites in the oral cavity. In addition, the efficacy of the active ingredient should not be diminished by any of the components of the vehicle in which it is contained.

Attempts to use antimicrobial surfactants in the past to control plaque formation (and the resultant deposition of calculus leading to gingivitis and periodontal disease) have not proven successful. For example, the antimicrobial agents, chlorhexidine and benzalkonium chloride cause deposition of adherent stains on the hard surfaces of teeth and/or dentures and prothese detracting from the possible utility of these agents in oral hygiene.

As indicated in U.S. Pat. Nos. 4,130,637 and 4,213,961 antimicrobial agents to be useful as aids in oral hygiene must inhibit plaque formation without staining. The antimicrobial agents of this disclosure are eminently suitable for oral hygiene preparations in that they control pathogens, help prevent plaque formation, do not cause objectionable staining, and indeed decrease the amount of staining caused by coffee, tea, other foods, and tobacco.

The compositions of this disclosure show multiple modes of action. They include but are not necessarily limited to:

1. inhibition of glycolysis by plaque and caries causing microorganisms;
2. bactericidal activity against oral pathogens at low ppm concentrations of active ingredient; and
3. inhibition of bacterial adhesion to tooth surfaces (augmented in the presence of salivary proteins responsible for pellicle formation on the teeth). Note: Without being committed to a specific theory, it is presumed that the latter unique characteristic is a likely reason for the sustained prevention of plaque adherence to tooth and prosthetic surfaces when C31G is combined with selected polishing agents and used as a dentifrice.

The following examples illustrate the concentrated formulations of compositions useful in various oral hygiene preparations.

EXAMPLE I

The composition described below is a concentrate of C31G*, an equimolar preparation of cocobetaine and cocoamine oxides (designations of CTFA Cosmetic and Toiletry and Fragrance Association, Wash., D. C.) [CTFA] which can be used in a number of different configurations to formulate a variety of mouthrinse, dentifrice as well as other suitable oral hygiene preparations.

C31G* is the name used for formulations of alkyl dimethyl glycines (betaines) and alkyl dimethylamine oxides as disclosed in U.S. Pat. No. 4,107,328. C31G is the preferred formulation of the invention, particularly when the alkyl dimethyl betaine and/or the alkyl dimethyl amine oxide contain 10-16 carbon atoms in the alkyl chain.

| | |
|---|---|
| Cocobetaine; 31.5% active ingredient (AI) | 405.5 lb |
| Cocamine oxide; 31.5% (AI) | 325 lb |
| Citric acid monohydrate, USP | 26 lb |
| Purified water, USP | 26 lb |
| To make about | 782.5 lb |
| C31G @ 29.6% AI | |
| At a dilution of 1% AI; pH = 4.9 | |

EXAMPLE II

The following composition is another example of a concentrate of C31G with an average alkyl chain length of $C_{14}$ and can be used to formulate a variety of different oral hygiene preparations.

| | |
|---|---|
| Myristamine oxide [CTFA] 50% | 105.6 lb |
| Citric acid monohydrate, USP | 10.2 lb |
| dissolved in $H_2O$ purified | 22. lb |
| Mixed at 50° with: | |
| Cocobetaine; 36% AI | 79. lb |
| Cetylbetaine; 25% AI | 86.4 lb |
| To make about | 303. lb |
| C31G @ 37.6% AI | |
| At a dilution of 1% AI; pH = 5.2 | |

In the following examples, concentrate formulations are prepared according to the procedures of the examples above using various mixtures and ratios of the amphoteric surfactants of components (a) and the T-amine oxide (b) at AI concentrations of 10-50% and are found to be satisfactory substitutions for the C31G concentrates of Examples III and IV. Protonating agents can be varied to give pH values suitable for each therapeutic and/or cosmetic value needed for oral hygiene applications as shown in the examples below.

EXAMPLE III-A

| | |
|---|---|
| Coco N amine propionic acid; 45% AI | 300 lb |
| Cocamine oxide; 25% AI | 540 lb |
| Citric acid monohydrate, ca. USP | 20 lb |
| Purified Water, USP | 10 lb |
| Citric acid is dissolved in 40° C. water and added to the mixed surfactants to effect a pH of 5.0 @ 1% AI | |
| To make about | 870 lb |
| = 31% AI | |

EXAMPLE III-B

| | |
|---|---|
| Coco amido N betaine 35% AI | 60 lb |
| Coco amido propylamine oxide 40% AI | 50 lb |
| Sodium phosphate, monobasic | 3.5 lb |
| Purified Water, USP | 20 lb |
| to make about | 133.5 lb |
| of concentrate @ 30.7% AI | |
| pH of 4.8 @ 1% AI | |

EXAMPLE III-C

| | |
|---|---|
| Coco N sulphobetaine 40% AI | 17 lb |
| 70/30 myristyl/palmitic-N,N dimethylamine 30% AI | 17 lb |
| Citric acid U.S.P. 30% | 1 lb |
| Water, purified | 5 lb |
| To make about | 40 lb |

-continued pH @ 30% AI = 5.3

EXAMPLE III-D

| | |
|---|---|
| 1-hydroxyethyl-1 carboxy methyl, 2-coco imidazalonium betaine 37% AI | 16.5 lb |
| 70/30 myristyl/palmitic-N,N dimethylamine oxide 30% AI | 16.5 lb |
| Buffered to pH 7.2 with: | |
| Sodium phosphate monobasic 1% | 2.0 lb |
| Sodium phosphate dibasic 1% | 1.0 lb |
| To make about | 35 lbs |
| at 31.6% AI | |

EXAMPLE IV

A mouthwash vehicle formulation was prepared for use with various dilutions of the C31G concentrate, as described in Example I.

| Mouthwash Vehicle | |
|---|---|
| Water, purified, USP | 13.5 g |
| Alcohol, USP 95% v/v* | |
| Sorbo Syrup USP 70% | 12.9 g |
| Sodium Saccharin, USP | 0.09 g |
| FDC Yellow #5 (1% in water) | 0.028 g |
| FDC Blue #1 (1% in water) | 0.028 g |

*Contains 0.09 artificial mouthwash flavor #6483 (Flavor Resources)

To this vehicle the C31G concentrate of Example I was added to prepare experimental mouthwashes having varied concentrations for the evaluations described below.

The following study was undertaken to determine the effect of C31G on oral pathogens. The data in Table I illustrates the activity of C31G at ppm concentrations ranging from 0.2 to 0.01% when used alone and in the presence of a mouthwash vehicle.

Note: The protocols involved in testing a wide variety of substances for their antimicrobial activities have been developed and utilized with special attention to their effects on periodontal pathogens. These systems, and in vitro procedures, have been applied to the study of C31G. It has been demonstrated that none of the vehicle components diminish the efficacy of C31G and that C31G is active at concentrations as low as 0.01% (equivalent to 100 ppm).

Gel Diffusion Studies

1) The activity of C31G, combined with the mouthwash vehicle, on Streptococcus sanquis was determined using a gel diffusion technique. Wells were made in agar (BHI-Difco or Tsoy-Difco) plates upon which had been spread a lawn of the bacteria. Aliquots of the test substances were placed in the wells and following incubation, their antimicrobial activities were assayed by measuring the radius of growth inhibition about each well. The dilutions are expressed as % active ingredients.

The results of this experiment are presented in Table 1.

TABLE 1

| Contents of Well | r Zone of Inhibition (Radius in mm) Strep. sanquis |
|---|---|
| 0.20% Chlorhexidine | 9 |

TABLE 1-continued

| Contents of Well | r Zone of Inhibition (Radius in mm) Strep. sanquis |
|---|---|
| 0.50% C31G in vehicle | 9 |
| 0.50% C31G | 9 |
| 0.30% C31G in vehicle | 9 |
| 0.30% C31G | 9 |
| 0.15% C31G in vehicle | 8 |
| 0.15% C31G | 7 |
| 0.10% C31G in vehicle | 8 |
| 0.10% | 8 |
| 0.05% C31G in vehicle | 7 |
| 0.05% C31G | 7 |
| 0.03% C31G in vehicle | 6 |
| 0.03% C31G | 5 |
| 0.01% C31G in vehicle | 2 |
| 0.01% C31G | |

2) The study described above was repeated using the gel diffusion method in order to examine the effects of C31G on a number of additional oral pathogens incriminated in the development of plaque and calculus formation. The gram-positive, aerobic pathogens contribute to the symbiotic colonization of gram-negative anerobic pathogens which can then lead to the onset of gingivitis and periodontal disease.

The results with five oral pathogens cited below. Including gram-positive, gram-negative, aerobic and anaerobic organisms are reported in Table 2.

1-*Streptococcus sanquis* (Gm+aerobic)
2-*Actinomyes viscosus* (Gm+aerobic)
3-*Bacteroides intermedius* (Gm—anaerobic)
4-*Capnocytophaga sputigens* (Gm—anaerobic)
5-*Actinobacillus actinomycetum comitans* (Gm—aerobic)

TABLE 2

Effect of C31G and other Mouthwash Formulations on Oral Pathogens

| Pathogen* | *Zone of Inhibition (radius in mm) | | | | |
|---|---|---|---|---|---|
| | 1 | 2 | 3 | 4 | 5 |
| Mouthwash Preparation | | | | | |
| Vehicle alone | 0 | 0 | 0 | 0 | 0 |
| C31G @ 0.2% AI | 7.5 | 11 | 10 | 6 | 4 |
| C31G @ 0.2% AI in mouthwash vehicle | 8.5 | 11 | 10.5 | 7 | 4 |
| Chlorhexidine @ 0.2% AI | 7 | 17 | 10.5 | 7 | 14 |
| Fluoroguard$^r$ | 0 | 0.5 | 0 | 0 | 0 |
| Listerine$^r$ | 0 | 0 | 0 | 0 | 0 |

MINIMUM INHIBITORY STUDIES

The C31G formulation when diluted and tested @0.05% AI, equivalent to 500 ppm actives, showed significant activity against all of the test pathogens.

The antimicrobial effects of C31G upon resting cells of *Strep. sanquis* were determined by exposing a standardized inoculum of bacteria to the mouthwash formulations. This was followed by transfer to fresh media. Following incubation, growth determinations were made spectrophotometrically in a Klett Summerson photoelectric colormeter (540 nm).

The concentrations of C31G were titrated against resting cells. The effects upon subsequent growth are presented in Table 3.

TABLE 3

| Agent | Klett Readings 24 hr. | Klett Readings 48 hr. |
|---|---|---|
| Saline | 135 | 142 |

TABLE 3-continued

| Agent | Klett Readings 24 hr. | Klett Readings 48 hr. |
|---|---|---|
| 0.2% Chlorhexidine | 0 | 0 |
| 0.5% C31G/vehicle | 0 | 0 |
| 0.5% C31G | 0 | 0 |
| 0.15% C31G/vehicle | 0 | 0 |
| 0.15% C31G | 0 | 0 |
| 0.05% C31G/vehicle | 0 | 0 |
| 0.05% C31G | 0 | 0 |
| 0.01% C31G/vehicle | 0 | 0 |
| 0.01 C31G | 0 | 0 |

EXAMPLE V

An accepted procedure for assaying the efficacy of oral hygiene products in the inhibition of pathogens that form plaque is the Stephan Index (R. J. Stephan-NIDR). In this example the effect of organisms in metabolizing sugars to lactic acid was assayed by the change of plaque pH after rinsing the oral cavity with a 10% sucrose solution. The normal pH of the oral cavity—and the plaque adhering to teeth—(in the absence of sugar—is 7.0. Within five minutes after a sugar challenge the pH of plague can free to below 5. (At this pH, tooth surfaces can dissolve and carries develop).

A mouthwash was prepared by diluting the C31G concentrate of Example II to 0.2% AI. Five students at a school for dental hygienists were exposed to the sugar challenge one hour after rinsing their mouths with distilled water. A baseline was established for each subject. It showed a pH decline to 1.32 units below the average pH of 7.1 within 5 minutes of the challenge (Standard Error 0.19 units).

The five subjects were instructed to rinse the oral cavity for 60 seconds with 10 ml of the above described C31G mouthwash. One hour later they were challenged with the sugar solution. Five minutes after the challenge the plaque pH had decreased by 0.9 pH units (S.E. = +0.24) a significant improvement of 32% over the control even though the sugar challenge took place one hour after the mouthwash procedure.

EXAMPLE VI*

*PAPER EXAMPLE

A mouthwash can be prepared by diluting the concentrate of Example III-A to 0.3% AI with purified water for use in the Stephen Index Study as in Example V.

As described in Example V the baseline Stephan Index for five subjects can be established. Ten ml of the above mouthwash can be used as an oral rinse for 30 to 60 seconds. One hour later the subjects can be exposed to the sucrose challenge solution and the drop in the pH determined after 5 minutes. The improvement in the Stephan Index expected is about 22%.

EXAMPLE VII*

*PAPER EXAMPLE

A mouthwash can be prepared by diluting the concentrate of Example III-B to 0.3% AI with a 0.1% solution of sodium fluoride for use in the Stephan Index as described in Example V.

The Stephan Index study can be repeated with the five subjects using 10 ml of mouthwash for 60 seconds. The improvement over the base level Stephan Index, after the subjects are exposed to the sucrose challenge solution, is expected to be about 34%.

EXAMPLE VIII*

*PAPER EXAMPLE

A mouthwash can be prepared by diluting the concentrate of Example III-C to 0.3% AI with purified water for use in the Stephan Index Study as described in Example V.

The Stephan Index baseline for five subjects can be established and 10 ml of the above mouthwash can be used as an oral rinse for 60 seconds. One hour later the subjects can be exposed to the sucrose challenge solution and the drop in the pH determined after 5 minutes. The improvement in the Stephen Index is expected to be about 34%.

EXAMPLE IX*

*PAPER EXAMPLE

A mouthwash can be prepared by diluting the concentrate of Example III-D to 0.3% AI with purified water for use in the Stephan Index study as described in Example V.

As in Example V the Stephan Index for baseline five subjects can be established and 30 ml of the above mouthwash can be used as an oral rinse for 30 seconds. One hour later the subjects can be exposed to the sucrose challenge solution and the drop in pH determined after 5 minutes. The improvement in the Stephan Index is expected to be about 28%.

EXAMPLE X

A laboratory assay of artificial plaque formation and adhesion as described by Kavanaugh et. al., (1974, J. Peridont. 45, 314-5) was performed to predict the effectiveness of G31G compounds in preventing bacterial adhesion to both root and enamel surfaces. The assay also was used to predict antiglycolytic effectiveness of the test product.

Freshly extracted teeth were cleaned, drilled through the root, and suspended on nichrome wires. The teeth and wires were sterilized in tubes containing water. Eight ml aliquots of trypticase soy broth were added to 2 ml aliquots of filtersterilized sucrose. Each tube was inoculated with 1 ml of a 24-hour culture of $Strep.$ $mutans$ 6715. The teeth were dipped in test compounds for 30 seconds, and then placed in the media described above. After incubation at 37° C. for 24 hours the tubes were redipped as before, and placed in fresh media, sucrose and inoculum. This procedure was repeated 24 hours later. Before each dipping the teeth were scored for plaque accumulation. Scoring involved grading the teeth from 0 to 3 according to the amount of plaque present on the wire, root, tooth and tube. Zero indicated no growth, 3 indicated heavy growth. After the last 24 hours of incubation (a total of 72 hours) the compounds were tested for their ability to metabolize glucose. The teeth were then removed from the inoculated media and placed in sterile media and sucrose, and incubated overnight at 37° C. for glycolysis studies.

The glycolysis assays were performed with the C31G formulation of Example I at concentrations of 0.1% and 0.5% actives as well as the individual components of C31G. Water was used as the negative control and a commercial mouthwash, Cepacol', which contains cetyl pyridinium chloride, was included as a positive control. The latter compound is known to be active in oral prophylaxis but is of the class that contributes to tooth staining. The results of the plaque accumulation in mg and the inhibition of glycolysis, as measured by pH, are shown in Table 4 below.

TABLE 4

| Compound | Ave. Wt. Plaque (mg.) | pH (glycolysis) |
| --- | --- | --- |
| C31G 0.5% AI (Example I) | 2 | 6.8 |
| C31G 0.1% AI (Example I) | 15 | 5.6 |
| Cocamine oxide 0.1% | 19 | 4.7 |
| Cocobetaine 0.1% | 22 | 5.0 |
| Cepacol | 7 | 6.4 |
| Water | 32 | 4.5 |

The above experiment demonstrated the effect of C31G in controlling plaque formation and adhesion as well as inhibiting glcolytic activity in formation of acid from sucrose. The components of C31G used separately were not as effective as the synergistic combination of the surfactants contained in C31G.

EXAMPLE XI

Twenty persons (10 male and 10 female) with varying amounts of dental plaque were given prophylactic treatments by a dental hygienist. Tooth color, and plaque were noted by the supervising doctor before and after treatment. The subjects were supplied with the mouthwash vehicle of Example III containing C31G (of Example I) at 0.25% AI and instructed to use the C31G mouthwash twice a day in addition to their normal toothbrushing. The subjects were monitored for plaque formation and tooth staining once a week for three weeks.

At the end of the trial period all subjects showed minimal plaque formation and no tooth staining-a common problem when cationic antiplaque agents such as chlorhexidine and benzalkonium chloride are used. An example of the cationic germicidal staining problem is described by Yankel, et al (J. Dent. Res. 61 1089-1093 (1982) who used chlorhexidine as a positive control agent to measure the amount of staining produced by agents used to help control plaque and gingivitis.

EXAMPLE XII

The following experiment was designed to obtain information related to the effect of C31G and related agents (when used in oral hygiene formulations) on inhibition of plaque formation and bacterial adherence to tooth surfaces. The in vitro model system was based upon the work of Rosan, et al, (Infection and Immunity 35 86-90, 1982).

Materials

[$^3$H] Thymidine labeled.—*Streptococcus sanquis* M-5
Hydroxyapatite [HA]
Saliva-treated hydroxyapatite (SHA)

Studies of bacterial adherence in vitro used a model system with HA beads and radiolabeled *Strep. sanquis*. To distinguish between specific and nonspecific binding, assays were carried out with HA and SHA. A series of experiments was conducted to determine the adherence of *Strep. sanquis* to HA and SHA in the presence or absence of C31G.

The results of specific and nonspecific binding in the competition assays are as follows:

1. C31G had a very significant effect on specific binding of *Strep. sanquis*/SHA as shown in the decrease of binding from 6% in the absence of C31G to 0.5% in the presence of C31G at 5% AI.

2. The effect of C31G on non-specific binding (*strep. sanguis*/HA) is minimal. 3. The effect of C31G on bacterial adhesion shows a dose response effect over the concentration range of 0.5%-5%. A typical result is shown the Graph.

It should be noted that decrease of adhesion of bacteria to tooth surfaces (hydroxyapatite/HA) is minimal in the absence of saliva. In the presence of saliva, adherence activity can be increased greater than 4000 fold depending upon the individual saliva sample. These adherence-providing proteins are deposited as the tooth pellicle within minutes on new HA surfaces. The use of the dentifrice examples (C31G type agents combined with a polishing agent) result in long-term inhibition of plaque formation. This synergistic activity is presumed to result from the effect of C31G in modifying the newly formed pellicle on the tooth surface as well as the compound's absorption to bacteria, thereby preventing adhesion.

This activity is indicated in the clinical data shown below. Incorporation of C31G in a dentifrice inhibited the accumulation of plaque for periods of 24-48 hours. Subsequent formation of calculus and staining also were inhibited as long as the dentifrice containing C31G was used.

EXAMPLE XIII

Dentifrice Formula

| Carbowax 400 [PEG 8] | 240 g |
| --- | --- |
| Methocel E4M [Hydroxyethyl cellulose] | 100 g |
| Water, Purified USP | 1300 g |
| Sodium Saccharin USP | 214 g |
| C31G conc. of Ex. II | 138 g |
| Peppermint flavor | 0.2 g |
| Calcium pyrophosphate | 2000 g |

The dentifrice is milled to a smooth paste and packaged in 100 g tubes. The pH of the dentifrice is 5.25 when measured at the glass electrode.

The above dentifrice was used by 20 subjects. Initially each subject used a commercial preparation (Crest formulation without pyrophosphate) containing an anionic surfactant. Evaluation for plaque accumulation was made by visualization of plaque formation after a 24-hour period following tooth brushing.

A base line was established by having the subjects submit to cleaning by a dental hygienist 24 hours before of the toothpaste was used. The plaque index was determined by visualization with sodium fluorescein and U.V. (Plaklite (r)=0.1 after cleaning.

Subsequent to establishing the base line, the subjects brushed their teeth with the control toothpaste (Crest group). After evaluation, the subjects brushed then their teeth with the dentifrice of Example XII.

After the subjects rinsed their mouths with water, followed by rinsing with a solution of sodium fluorescein, the surfaces of the teeth were photographed with ultraviolet light and the plaque accumulation scored by or stating the percent of the tooth surfaces stained by the fluorescent dye.

The reduction of plaque accumulation from the 24-hour baseline (100% under the conditions of this study) was estimated to have decreased to an average of 21.3% for the Crest group (after 24 hrs.) and 0.9% for the subjects using the dentifrice formula of Example XII. After an additional 24-hours without toothbrushing, the average fluorescent dye staining scores had increased to but 4.6% in the subjects using the C31G dentifrice formulation. The improvement compared with the commercial toothpaste, (over 95% for 24 hours after toothbrushing) was maintained at an 80% level for an additional 24 hours.

EXAMPLE XIV

This is an example of a two-part dentifrice:

| | |
|---|---|
| a) Calcium pyrophosphate - (Monsanto soft) packaged in 4 oz. plastic cups-yield 430 cups. | 12.0 kg, |
| b) C31G (Example I) 30% AI | 1 kg |
| Water, purified, USP | 11 kg |
| Sodium saccharin, USP | 0.24 kg |

Packaged 4-oz. dispensing bottles with a yield of 430,4-oz. containers.

Six volunteer subjects were instructed to use the above dentifrice according to their usual daily tooth brushing habits. The instructions included the wetting of the bristles of the toothbrush with solution (b) and dipping and redipping the moistened toothbrush to collect the powder (a) for brushing the tooth surfaces. The subjects were also told to re-moisten the bristles after brushing the lingual surfaces and re-wetting for brushing of the buccal surfaces. The ages of the subjects (3 male and 3 female) ranged from 30-70 yrs. Three subjects in the group smoked more than 30 cigarettes per day.

Plaque, staining and gingival inflammation indices were recorded by the subjects' dentists before initiating the trial and again 90 days after the trial period. The average consumption of test materials was ca, 7 gm per day of powder and 7 gm per day of liquid.

At the end of the test period all indices had improved as shown in Table 5 below.

TABLE 5

| AVERAGE INDICES AFTER 90 DAYS DENTIFRICE USE | | | |
|---|---|---|---|
| | PlI$^a$[Range] | GI$^b$[Range] | SI$^c$[Range] |
| Baseline$^d$ | 1.5 [1.2–2.3] | 1.2 [0.8–1.2] | 33 [10–75] |
| Two-part dentifrice | 0.5 [0.1–0.7] | 0.2 [0.1–0.3] | 5 [0.5–10] |

Notes:
$^a$PLI - Plaque Index (Silness & Loe) - 1964, Acta Odont Scan 22, 121).
$^b$GI - Gingival Index (Loe & Silness - 1963, Acta Odont Scan 21, 533).
$^c$SI - Stain Index - % of tooth surface showing staining greater than standard artificial teeth.
$^d$Baseline - Result of examination before initiating trial and after routine use of commercial dentifrice for 90 days.
*The unstained areas of all teeth were lighter in color than the standard artificial teeth.

All indices showed significant improvement. The control of plaque formation resulted in almost no calculus being deposited in the gingival area. This was probably a major reason for the dramatic improvement in the gingival index.

One subject had a crown installed just prior to the test period. The crown was made to match what appeared to be the normal color of her teeth after prophylaxis. Thirty days after using the C31G dentifrice the color of the natural teeth was significantly lighter than the color of the newly installed crown.

All three smokers reported a marked decrease in nicotine (tar) staining to which smokers are accustomed. This is notable as the calcium pyrophosphate is rated as a low abrasion polishing agent. The stain reduction can only be attributed, therefore, to the presence (activity) of C31G.

The following examples indicate the sensitivity of the optimum of dentifrice formulations to compatability with polishing agents.

The useful abrasive or polishing agents that enhance the effectiveness of "C31G" and equivalent formulations and may be considered silica equivalents, have the following characteristics: they should be inert to the surfactant components; insoluble in the aqueous buffer solutions in the pH range of 4.2–7.0; and not contain reducing agents or heavy metal impurities which may catalyze the deoxygenation of the T-amine oxides. The radioactive dentine abrasiveness (RDA) is preferably in the range of 500–1000, which produce dentifrices of normal abrasiveness, after formulation, of about 200 RDA for routine use.

EXAMPLE XVI

The dentifrices described below were formulated to examine the effect on the plaque index of various polishing agents when combined with C31G; the dentifrices were prepared and packaged in plastic tubes, stored for thirty days at ambient temperatures (18°–23° C.) and then used in the following protocol.

Six subjects were issued a commercial dentifrice (D) and were instructed to brush their teeth once a day for seven days. At this time the plaque index (Silness & Loe, 1964) was determined. The subjects were then issued experimental toothpastes A, B, or C and instructed to use the dentifrice brushing their teeth once a day for five days. At this time the plaque index was again determined.

The subjects used no oral hygiene for 24 hours after day five. The plaque index was determined again on day six to measure the persistance of inhibition of plaque formation and/or adherence.

Dentifrice Formulations

| | Dentifrice | | | |
|---|---|---|---|---|
| Components in % | A | B | C | D* |
| Cellulose Gum 5% gel [CMC-7MF, Hercules] | 2.1 | 2.1 | 2.1 | |
| Saccharin USP | 0.35 | 0.35 | 0.35 | |
| Sorbitol 70% USP | 17.3 | 17.3 | 17.3 | |
| Silica, Colloidal [HSG 750 Grace] | 25.0 | 25.0 | 25.0 | |
| Calcium Pyrophosphate | 30.2 | — | — | |
| Calcium Carbonate ppt USP | — | 30.0 | — | |
| Aluminum Hydroxide | — | — | 30.0 | |
| Spearmint Flavor [20.240 Flavor Key] | 0.25 | 0.25 | 0.25 | |
| Peppermint Flavor [20.210] Flavor Key | 0.05 | 0.05 | 0.05 | |
| C31G Conc. of Example 1 30% AI | 4.0 | 4.0 | 4.0 | |
| Water, purified USP | 20.0 | 20.0 | 20.0 | |

*Formulation D is a commercial toothpaste containing 1% sodium lauryl sulphate as the surfactant.

TABLE 6

Effects of the use of the Dentifrice Formulations of Example XVI on the Growth and Adherence of Plaque

| | Plaque Index* After Use Of Dentifrice Time of Evaluation | | | |
|---|---|---|---|---|
| | A | B | C | D |
| Day 0 | 1.05(0.31) | 0.95(0.36) | 1.10(0.40) | 1.12(0.45) |
| Day 5 | 0.18(0.05) | 1.24(0.63) | 1.18(0.49) | 1.20(0.50) |
| Day 6 | 0.28(0.09) | 2.15(1.02) | 1.70(0.63) | 1.95(0.75) |
| pH of dentifrice | 5.20 | 9.1 | 7.9 | 7.3 |

TABLE 6-continued

Effects of the use of the Dentrifice Formulations of
Example XVI on the Growth and Adherence of Plaque

| | Plaque Index* After Use Of Dentrifice Time of Evaluation | | | |
|---|---|---|---|---|
| | A | B | C | D |
| on Day 0 | | | | |

*Silness and Loe, 1964
()Standard Deviation n = 6

The results shown in Table 6 demonstrate a very significant improvement of composition A in the range of 80-90% [p 0.001] over compositions B, C, and D. This is an especially noteworthy result in that the use of composition A, with no oral hygiene, resulted in a persistant inhibition of plaque accumulation for 24 and more hours. This surprising effect is not noted in the absence of a polishing agent which has an abrasive effect in removing pellicle from the tooth surface in the presence of C31G. Since the activity of C31G is not altered by changes in pH or other effects, such compositions have an extraordinary usefulness in maintaining oral health.

EXAMPLE XVII

A significant problem may develop as a result of oral prostheses, such as dentures, where the patient is fitted with removable, partial or full plates that occlude areas of the palate and gums. Food particles and other salivary debris as well as microorganisms, trapped between soft tissue and a prosthesis, can result in irritation predisposing the affected site to infection. In the absence of infection an inflammatory response is evidenced by edema and erythema in the occluded areas, particularly on the hard palate. Malodor is another frequently encountered problem).

Infections (stomatitis) are frequently caused by such oral microflora as the fungus, *Candida albicans*. C31G and other formulations of this invention in the range of 0.01-0.2% AI are active against *C. albicans*, and other fungal as well as bacterial pathogens.

The effect of C31G compositions were studied on two volunteer subjects who had been fitted with partial upper dentures which occluded 30 to 50% of the hard palate as well as other soft tissue. The subjects experienced signs of inflammation whenever their denture were worn for a full 24-hour cycle. This in spite of daily cleaning procedures with commercial solutions or conventional dentifrice preparations.

Both subjects initiated a once-a-day program of oral and dentures hygiene using the two-part dentifrice of Example XIV. The regimen made it possible for them to wear their dentures throughout a 24-hour period.

After one week of C31G use clinical examination showed that edema and erythema were absent. The subjects also reported an increase of comfort and absence of malodor. Upon their return to routine use of commercial cleaning solutions edema and erythema returned within 2-3 days. Further studies showed that brushing with the liquid phase of Example XIV without the polishing agent was not effective. The subjects continued their use of the Example XIV dentifrice for an additional 90 days. Checking the dentures during this period showed a significant decrease of staining and tartar accumulation and clinical examination confirmed the absence of inflammation. Use of the liquid without a polishing agent alone, however, in conjuction with a high intensity ultrasonic field produced satisfactory results when the denture was subsequently introduced to the oral cavity in the presence of C31G liquid.

EXAMPLE XVIII

In more advanced cases of gingivitis and periodontitis, the recommended therapy is often surgical intervention. Studies were undertaken to determine the effects of irrigation with solutions of C31G to indicate whether control of subgingival pathogens could decrease the need for radical periodontal procedures.

The following composition of C31G was prepared.

| Oral Irrigation Formulation HC12 | |
|---|---|
| Water, purified | 532.9 grams |
| Sorbitol 70% USP | 128.5 grams |
| Saccharin USP | 3.6 grams |
| C31G, 30% AI [Example I] | 333.4 grams |
| Flavor #6483 [Flavor Key] | 1.6 grams |
| To make about | 1 liter |
| At a concentration of 10% AI; pH 4.85 @ 1% AI | |

Three volunteer subjects with advanced gingivitis and periodontal disease underwent an oral examination and routine cleaning of the teeth. This procedure included removal of supra and subgingival calculus. The patients were then instructed to undertake a regimen of tooth and gum irrigation in conjuction with their normal oral hygiene activities which included the use of a dentifrice, flossing and gum massage. (No surgical intervention was initated during the study). The following irrigation protocol was used.

IRRIGATION PROTOCOL

Unless otherwise noted two teaspoons (10 grams) of the irrigation solution HC12 were mixed with 12 oz. of water (0.25% AI) for use with a Water Pik[r] at a recommended setting of 5—range available 1-10, and a pulsating stream of the solution was delivered for a period of 90-120 seconds. The subjects were instructed to direct the stream at an angle perpendicular to the plane of the tooth surface at the gingival junction with the the teeth.

Following are the case histories of the three subjects.

SUBJECT #1

Day 0—Gingival Index: 3 (Loe & Silness, 1963) Ibid.

At the outset this patient had significant, unstimulated bleeding on the gingival crevices adjacent to three lower incisors. Gingival crevice depths were in the range of 7-10 mm. Two incisors had draining fistulae below the gingival line which were subjected to an initial treatment consisting of irrigation of the pockets with a one ml tuberculin syringe containing solution HCl2 diluted to 1% AI with purified water. The needle of the syringe was carefully inserted into the gingival crevice along the surface of dentine so as not to penetrate soft tissue. The orthodontist then irrigated the pockets and fistulae with 1 ml of the diluted HCl2 solution in each of the two pockets.

Following this regimen the patient was instructed to initiate to daily irrigation procedures according to the Protocole described above.

Day 1—Gingival Index: 2.0

Gingival condition apparently improved with less swelling and redness noted. Fistulae no longer draining.

Day 4—Gingival Index: 1.5

Some exudate with squeezing. No suppuration or swelling noted.

Day 21—Gingival Index: 0.5

Considerable clinical improvement. No visible fistulae or swelling. Color and strippling normal.

Day 90—Gingival Index: 0

Improvement maintained. Color of gingival tissues good. Pockets persist but show no exudate on pressure with a blunt instrument. Gums firm; gingival margins are normal. Pockets present but show no signs of bleeding.

SUBJECT #2

Day 0—Gingival Index: 2.5

Some spontaneous bleeding. All affected teeth show bleeding on probing. Gingiva inflammed. Irrigation protocol initiated.

Day 14—Gingival Index: 1.3

Considerable clinical improvement. Some pockets show bleeding on probing. Gingiva show a colorless exudate; slightly reddened at the margin.

Day 90—Gingival Index: 0

Gingiva firm; pale pink in color with normal strippling. Gingival margin rounded but occluded to the tooth surface. Pockets evident only on probing. No exudate present.

SUBJECT #3

Day 0—Gingival Index: 2.2

Gingiva in affected areas moderately inflamed, and swollen. Slight bleeding in some pockets with probing. Irrigation protocol initiated.

Day 14—Gingival Index: 1.2

Considerable clinical improvement. Erythema and edema restricted to gingival margins. Bleeding not evident on pressure with a blunt instrument. Slight, colorless exudate evident.

Day 60—Gingival Index: 0

Gingiva appears normal: pink and firm with no evidence of exudate. Gingival margin rounded and occluded to the tooth surface. A gingival crevice is present but shows no signs of infection.

We claim:

1. A process for enhancing oral hygiene by reducing oral microflora and for inhibiting the formation of dental plaque in a subject which comprises the step of: applying to the oral cavity a composition consisting essentially of a) 0.1 to 40 parts, by weight, of a higher acyl-N-betaine having the structure

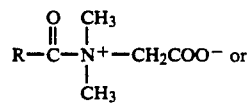

or

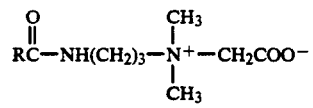

where R is a higher alkyl group of from 10 to 18 carbon atoms and b) 0.1 to 40 parts, by weight, of a higher alkyl-N,N-dimethylamine oxide, a higher alkyl-N,N-dihydroxylethylamine oxide, or an acylamido t-amine oxide having the respective structures:

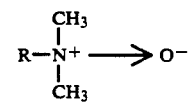

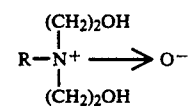

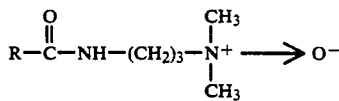

wherein R is a higher alkyl of from 10 to 18 carbon atoms, or mixtures of amine oxides; and c) acid in an amount sufficient to adjust the pH of the composition from 4.2 to 7.5 when measured in an aqueous solution of components (a) and (b) in an orally acceptable carrier.

2. A process, as in claim 1, wherein the acid used to adjust the pH is selected from the group consisting of hydrochloric, phosphoric, sulfuric, citric, acetic and nicotinic acid.

3. A process, as in claim 1, wherein the acid is added in an amount sufficient to adjust the pH of the composition from 4.5 to 7.0.

4. A process, as in claim 3, wherein the acid is added in an amount sufficient to adjust the pH of the composition from 4.5 to 6.5.

5. A process as in claim 4, wherein the acid is added in an amount sufficient to bring the pH to pH 4.8.

6. A process, as in claim 1, wherein the composition further comprises an inert polishing agent.

7. A process, as in claim 6, wherein the polishing agent is one selected from alumina, aluminum silicate, zeolites, calcium pyrophosphate, dicalcium acid phosphate, and kaolin.

8. A process, as in claim 6, wherein the orally acceptable carrier contains 15–60% by weight of the polishing agent.

9. The process, as in claim 1, wherein the composition is used in conjunction with an ultrasonic device having a high intensity field, for cleaning oral prosthesis.

10. The process as in claim 1, wherein the composition is applied to the oral cavity by rinsing the mouth, or brushing the teeth.

* * * * *